United States Patent
Kessler et al.

(10) Patent No.: US 10,241,085 B2
(45) Date of Patent: *Mar. 26, 2019

(54) SCANNING ACOUSTIC MICROSCOPE WITH AN INVERTED TRANSDUCER AND BUBBLER FUNCTIONALITY

(71) Applicant: Sonoscan, Inc., Elk Grove Village, IL (US)

(72) Inventors: Lawrence W. Kessler, Buffalo Grove, IL (US); Thomas Kleinschmidt, Prospect Heights, IL (US); Dan Micek, Norridge, IL (US)

(73) Assignee: Nordson Corporation, Westlake, OH (US)

( * ) Notice: Subject to any disclaimer, the term of this patent is extended or adjusted under 35 U.S.C. 154(b) by 191 days.

This patent is subject to a terminal disclaimer.

(21) Appl. No.: 15/186,879

(22) Filed: Jun. 20, 2016

(65) Prior Publication Data

US 2016/0290968 A1    Oct. 6, 2016

Related U.S. Application Data

(63) Continuation of application No. 14/216,429, filed on Mar. 17, 2014, now Pat. No. 9,377,443, which is a continuation of application No. 13/304,070, filed on Nov. 23, 2011, now Pat. No. 8,720,273.

(60) Provisional application No. 61/416,610, filed on Nov. 23, 2010.

(51) Int. Cl.
*G01N 29/265* (2006.01)
*G01N 29/28* (2006.01)
*G01N 29/06* (2006.01)

(52) U.S. Cl.
CPC ....... *G01N 29/0681* (2013.01); *G01N 29/265* (2013.01); *G01N 29/28* (2013.01); *G01N 2291/101* (2013.01); *G01N 2291/2697* (2013.01)

(58) Field of Classification Search
CPC .. G01N 29/0681; G01N 29/28; G01N 29/265; G01N 2291/101; G01N 2291/2697
USPC .......................................................... 73/606
See application file for complete search history.

(56) References Cited

U.S. PATENT DOCUMENTS

| | | | | |
|---|---|---|---|---|
| 4,378,699 | A | * | 4/1983 | Wickramasinghe ........................ G01N 29/0681 73/606 |
| 4,646,573 | A | * | 3/1987 | Stoll ....................... G01H 3/125 73/606 |
| 8,720,273 | B2 | * | 5/2014 | Kessler .............. G01N 29/0681 73/606 |
| 9,170,236 | B2 | * | 10/2015 | Kessler .............. G01N 29/0681 |
| 9,377,443 | B2 | * | 6/2016 | Kessler .............. G01N 29/0681 |
| 2006/0081051 | A1 | * | 4/2006 | Kessler .................. G01N 29/06 73/618 |

* cited by examiner

*Primary Examiner* — J M Saint Surin
(74) *Attorney, Agent, or Firm* — Baker & Hostetler LLP

(57) ABSTRACT

A scanning acoustic microscope includes a transducer mounted below a particular elevation and configured to produce ultrasonic energy, a coupling fluid source configured to introduce coupling fluid between the transducer and the particular elevation. Ultrasonic energy is directed upwardly through coupling fluid disposed between and the transducer and a first surface of a part to be inspected, wherein the part is disposed at the particular elevation and wherein a second surface of the part is not contacted by coupling fluid during inspection.

23 Claims, 2 Drawing Sheets

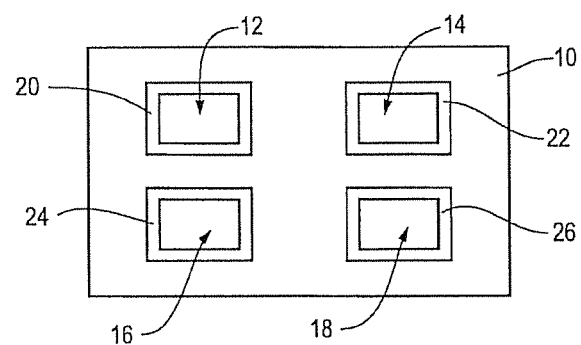
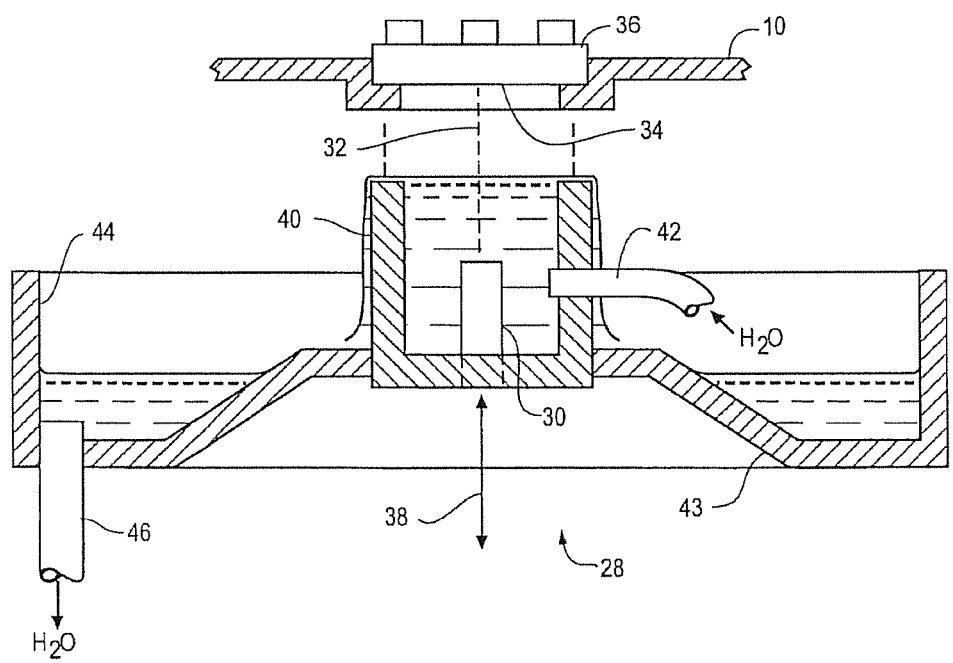

SCANNING ACOUSTIC MICROSCOPE WITH AN INVERTED TRANSDUCER AND BUBBLER FUNCTIONALITY

CROSS REFERENCE TO RELATED APPLICATIONS

This application is a continuation of U.S. patent application Ser. No. 14/216,429, filed Mar. 17, 2014; which is a continuation of U.S. patent application Ser. No. 13/304,070, filed Nov. 23, 2011, issued as U.S. Pat. No. 8,720,273 on May 13, 2014; which claims the benefit of U.S. Provisional Patent Application No. 61/416,610, filed Nov. 23, 2010. The entire contents of these applications are hereby incorporated by reference.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present invention relates to a scanning acoustic microscope with an inverted transducer and bubbler functionality for inspecting a part.

2. Description of the Background of the Invention

U.S. Pat. No. 7,584,664 is entitled "acoustic micro imaging device having at least one balanced linear motor assembly." U.S. Pat. No. 7,522,780 is entitled "frequency domain processing of scanning acoustic imaging signals." U.S. Pat. No. 7,395,713 is entitled "tray-fed scanning microscope system and method primarily for immobilizing parts during inspection." U.S. Pat. No. 7,000,475 is entitled "acoustic micro imaging method and apparatus for capturing 4D acoustic reflection virtual samples." U.S. Pat. No. 6,981,417 is entitled "scanning acoustic micro imaging method and apparatus for non-rectangular bounded files." U.S. Pat. No. 6,895,820 is entitled "acoustic micro imaging method and apparatus for capturing 4D acoustic reflection virtual samples." U.S. Pat. No. 6,890,302 is entitled "frequency domain processing of scanning acoustic imaging signals." U.S. Pat. No. 6,880,387 is entitled "acoustic micro imaging method providing improved information derivation and visualization." U.S. Pat. No. 6,460,414 is entitled "automated acoustic micro imaging system and method." U.S. Pat. No. 6,357,136 is entitled "scanning acoustic microscope system and method for handling small parts." U.S. Pat. No. 5,684,252 is entitled "method and apparatus for ultrasonic inspection of electronic components." U.S. Pat. No. 5,600,068 is entitled "controlled-immersion inspection." U.S. Pat. No. 4,866,986 is entitled "method and system for dual phase scanning acoustic microscopy." U.S. Pat. No. 4,781,067 is entitled "balanced scanning mechanism." U.S. Pat. No. 4,518,992 is entitled "acoustic imaging system and method." U.S. Patent Application Pub. No. 20090095086 is entitled "scanning acoustic microscope with a profilometer function." U.S. Provisional Application Ser. No. 61/362,131 is entitled "acoustic micro imaging device with a scan while loading feature." The contents of all of the aforementioned patents, publications and applications are incorporated by reference into this application as if fully set forth herein.

SUMMARY OF THE INVENTION

According to one aspect, a scanning acoustic microscope includes a transducer and a coupling fluid source. The transducer is mounted below a particular elevation and configured to produce ultrasonic energy, and the coupling fluid source is configured to introduce coupling fluid between the transducer and the particular elevation. Ultrasonic energy is directed upwardly through coupling fluid disposed between and the transducer and a first surface of a part to be inspected, wherein the part is disposed at the particular elevation and a second surface of the part is not contacted by coupling fluid during inspection.

According to another aspect, a scanning acoustic microscope includes a transducer, a coupling fluid source, and a controller. The transducer is disposed below a particular elevation, and the coupling fluid source is disposed below the particular elevation and configured to introduce coupling fluid between the transducer and the particular elevation. The controller is operable to control the coupling fluid source and the transducer such that coupling fluid from the coupling fluid source is directed upwardly to reach a first portion of a part disposed at the particular elevation and not contact a second portion of the part, and ultrasonic energy from the transducer is directed upwardly through the coupling fluid.

According to yet another aspect, a method of inspecting a part using a scanning acoustic microscope includes the steps of disposing a transducer below a particular elevation, controlling a coupling fluid source to direct coupling fluid upward to at least the particular elevation, and operating the transducer to direct ultrasonic energy upward through the coupling fluid to inspect the part. During inspection of the part, the coupling fluid contacts a first portion of the part disposed at the particular elevation and does not contact a second portion of the part disposed above the particular elevation.

BRIEF DESCRIPTION OF THE DRAWINGS

Various examples objects, features and attendant advantages of the present invention will become fully appreciated as the same becomes better understood when considered in conjunction with the accompanying drawings, in which like reference characters designate the same or similar parts throughout the several views, and wherein:

FIG. 1A is a top view of a tray of parts that is designed to support various large microelectronic samples for transport through a scanning acoustic microscope illustrated in the remaining figures;

FIG. 1B is a side view, partly in cross section, of a portion of an embodiment of a scanning acoustic microscope having an inverted transducer and a bubbler functionality;

DETAILED DESCRIPTION OF THE PREFERRED EMBODIMENTS

Figure 2:
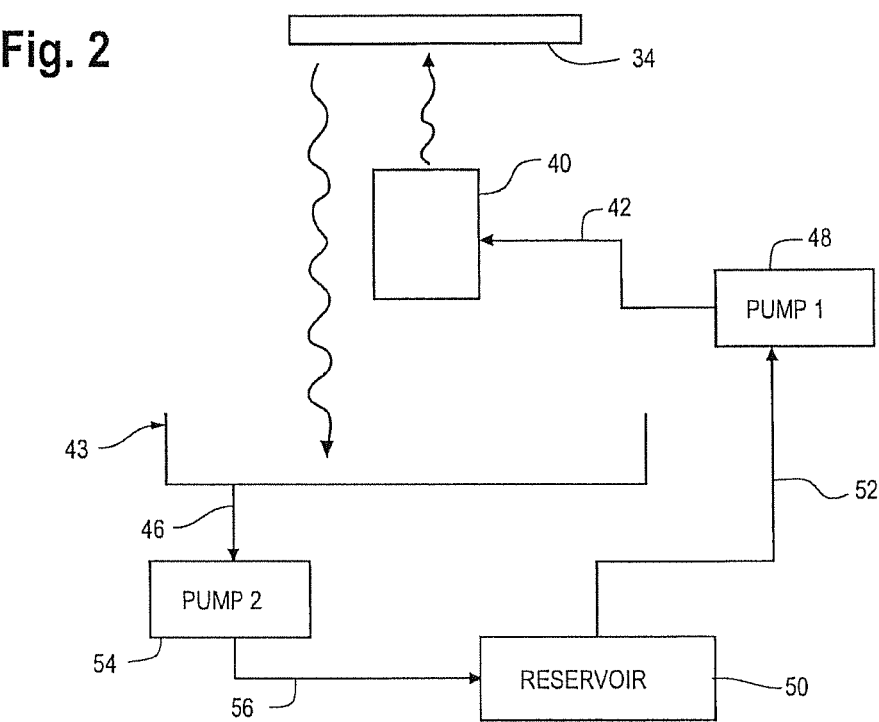
FIG. 2 is a combined diagrammatic view and block diagram showing the transport of coupling fluid through the microscope of FIG. 1B.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated. It should be further understood that the title of this section of this specification, namely, "Detailed Description of the Preferred Embodiments" relates to a requirement of the United States Patent Office, and does not imply, nor should be inferred to limit the subject matter disclosed herein.

In the present disclosure, the words "a" or "an" are to be taken to include both the singular and the plural. Conversely, any reference to plural items shall, where appropriate, include the singular.

The description in this document concerns a scanning acoustic microscope having an inverted transducer and a bubbler feature. It is the applicants' intention to preserve the ability to claim a device that includes an inverted transducer and a bubbler feature in combination with none, any, some or all of the other acoustic microscopy features disclosed in the patents and other information incorporated by reference into this document as if fully set forth herein as noted in the background of the invention section.

FIG. 1A is a top view of a tray 10 that is designed to support a number of large microelectronic samples for transport through a scanning acoustic microscope having an inverted transducer and a bubbler feature. In the illustrated embodiment, tray 10 includes four part support areas 12, 14, 16 and 18 that are defined by ledges 20, 22, 24 and 26. A suitable target such as, for example, a microelectronic sample part 36 (shown in FIG. 1B) can be supported on the ledges 20-26 within the support areas 12-18 of the tray 10.

FIG. 1B is a side, partial cross sectional view of a portion of an embodiment of a scanning acoustic microscope 28 having an inverted transducer and a bubbler functionality. Scanning acoustic microscope 28 includes a waterproof ultrasonic transducer 30 that is designed to emit pulses of ultrasonic energy along axis 32 towards an underside 34 of a sample part 36 that, in use, is generally opposite to the force of gravity. An outer portion of sample part 36 rests on one of the ledges 20-26 defining one of the part support areas 12-18 in tray 10. Transducer 30 is connected to suitable control circuitry (not shown) via line 38.

In the illustrated embodiment of the invention, transducer 30 is secured to a bottom surface of a spray cup 40 by, for example, a threaded connection. A water inlet tube 42 is inserted through a side aperture in spray cup 40 with sufficient pressure to allow water (or any other suitable coupling fluid) to fully immerse the transducer 30 inside of spray cup 40 and then travel upwards in a laminar flow (so that bubbles or entrained air do not form in the flow, at least until the water deflects off the part) and contact the underside 34 of sample part 36. One aspect of the invention is that, for example, the water pressure is sufficiently high to cause a water flow to cover the distance between the end of the spray cup 40 and the underside 34 of the sample part 36 without blowing the part 36 off of the tray 10 if the water pressure were too high. As discussed in greater detail hereinafter, the appropriate water pressure for a given application can be determined by visual inspection and then set and thereafter automatically applied for subsequent acoustic microscopic inspection of trays of parts as they are moved into and then out of the scanning acoustic microscope 28. Furthermore, it is may be preferable (depending upon, among other things, coupling fluid supply pressure) that a gap be maintained between the sample part 36 and the spray cup 40 to prevent water pressure from becoming too high such that the water pressure causes the part to be lifted off of the tray 10.

In addition, the sample part 36 may have a critical and non-critical side wherein the critical side cannot get wet. To prevent water from seeping up around the ledges 20-26 during the inspection of the non-critical side, a fan or air knife can be used to blow air toward the critical side of the sample part 36. The fan or air knife is preferably located above the tray 10 and scanning microscope 28 and may be of sufficient capacity to generate a stream of air that covers the entire tray 10. Alternatively, the fan or air knife may cover only a single part 36 or portion of a part, for example the edges(s) of a part 36, as desired. The fan or knife blower may also be used to maintain the sample part 36 in place if the pressure of the water flow increases.

Another feature of the invention disclosed herein involves the utilization of a drain saucer 43 that, in an exemplary embodiment of the invention, is connected to an outer and lower external surface of spray cup 40. The drain saucer 43 includes a raised outer rim 44 that is sufficiently wide to be able to capture all of the water emitted from the spray cup as it splashes off of the sample part 36 and the tray 10 and falls back towards the drain saucer 43 due to the force of gravity. A drain tube 46 is inserted in an aperture formed in a bottom portion of drain saucer 43 that is shaped so that all water caught by the drain saucer 43 is directed towards the drain tube 46.

FIG. 2 is a schematic diagram showing the transport of water through the scanning acoustic microscope 28. An inlet pump 48 draws water from reservoir 50 via tube 52, pressurizes the water to a suitable level, and then provides the pressurized water to spray cup 40 via tube 42. A drain pump 54 draws water from the drain saucer 43 via drain tube 46 and then provides the collected water back to reservoir 50 via tube 56.

Figure 3:
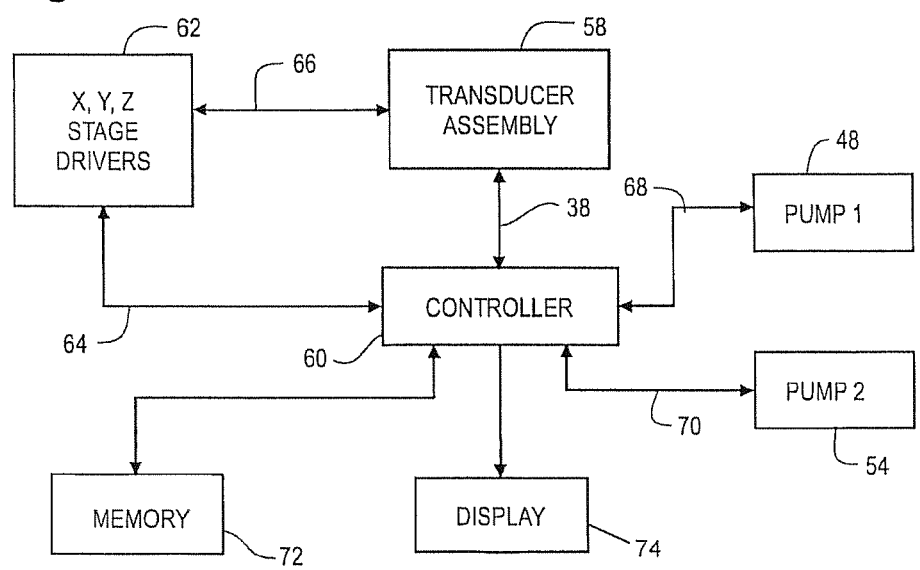
FIG. 3 is a block diagram showing the electrical connections of the microscope of FIG. 1B.

FIG. 3 is a schematic diagram showing the electrical connections of the scanning acoustic microscope 28. The transducer assembly 58 includes, in the illustrated embodiment, the transducer 30, the spray cup 40 and the drain saucer 43 shown in FIG. 1B. Electrical signals between, to, and from the transducer 30 to the controller 60 pass along line 38. Controller is electrically connected to x, y, z stage drivers 62 via line 64 so that the x, y, z stage drives can cause transducer assembly 58 to be moved in operative relation with respect to the tray 10 by means of actuators 66 to allow for non-destructive testing of the samples on tray 10 to take place. For example, this action can cause transducer 10 to be moved in an x-y raster scan of each sample.

Controller 60 also is electrically connected to pumps 48 and 54 via lines 68 and 70. The pumps 48 and 54 are turned on and off as needed for non-destructive testing purposes of samples disposed on the tray 10. Information about the scanning process and the scan results are caused to be shown on the display 74 by controller 60. For example, both time domain and frequency domain images of a particular sample can be appropriately color coded and then shown to an operator for analysis. Controller 60 is electrically connected to a memory 72 so that, if desired, data for scans can be stored for later analysis or retrieved therefrom and transmitted to others via suitable transport (e.g., email or a memory stick).

INDUSTRIAL APPLICABILITY

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A scanning acoustic microscope, comprising:
a transducer mounted below a particular elevation, the transducer being configured to produce ultrasonic energy; and
a coupling fluid source configured to introduce coupling fluid below the particular elevation, wherein:
a part to be inspected is disposed at the particular elevation,
the ultrasonic energy is directed upwardly through the coupling fluid between the transducer and a first surface of the part, and
a second surface of the part is not contacted by the coupling fluid during inspection.

2. The scanning acoustic microscope of claim 1, further including an air source disposed above the particular elevation, the air source being configured to blow air downwardly on the second surface of the part to be inspected.

3. The scanning acoustic microscope of claim 2, wherein the air source is a fan or air knife.

4. The scanning acoustic microscope of claim 1, further including a controller operable to control the transducer and the coupling fluid source during inspection.

5. The scanning acoustic microscope of claim 1, further including a pump for pressurizing the coupling fluid before the coupling fluid is introduced through the coupling fluid source.

6. The scanning acoustic microscope of claim 1, wherein the transducer is disposed in a container.

7. The scanning acoustic microscope of claim 6, wherein the container is a cup.

8. The scanning acoustic microscope of claim 4, further including a display operated by the controller for displaying inspection results.

9. A scanning acoustic microscope, comprising:
a transducer disposed below a particular elevation, the transducer being configured to produce ultrasonic energy;
a coupling fluid source disposed below the particular elevation, the coupling fluid source being configured to introduce coupling fluid below the particular elevation; and
a controller operable to control the coupling fluid source and the transducer such that the coupling fluid from the coupling fluid source is directed upwardly to reach a first portion of a part that is at the particular elevation and not contact a second portion of the part, and the ultrasonic energy from the transducer is directed upwardly through the coupling fluid.

10. The scanning acoustic microscope of claim 9, further including a part carrier configured to hold the part at the particular elevation.

11. The scanning acoustic microscope of claim 9, further including an air source configured to blow air downwardly on a surface of the second portion of the part.

12. The scanning acoustic microscope of claim 11, wherein the air source is a fan or air knife.

13. The scanning acoustic microscope of claim 9, further including a container, wherein the transducer is disposed in the container.

14. The scanning acoustic microscope of claim 13, wherein the container is a cup.

15. The scanning acoustic microscope of claim 9, further including a pump for pressurizing the coupling fluid before the coupling fluid is introduced through the coupling fluid source.

16. A method of inspecting a part using a scanning acoustic microscope, the method comprising:
introducing the part at a particular elevation above a transducer configured to produce ultrasonic energy;
controlling a coupling fluid source to direct coupling fluid upward to at least the particular elevation; and
operating the transducer to direct the ultrasonic energy upward through the coupling fluid to inspect the part,
wherein, during inspection of the part, the coupling fluid contacts a first portion of the part that is at the particular elevation and does not contact a second portion of the part that is above the particular elevation.

17. The method of inspecting the part of claim 16, wherein controlling the coupling fluid source includes pressurizing the coupling fluid.

18. The method of inspecting the part of claim 16, further including applying pressurized air downwardly on the second portion of the part during inspection.

19. The method of inspecting the part of claim 16, wherein operating the transducer includes driving the transducer along a scan path to inspect the part.

20. The method of inspecting the part of claim 16, further including displaying results of the inspection of the part on a display.

21. The scanning acoustic microscope of claim 1, wherein the coupling fluid is water.

22. The scanning acoustic microscope of claim 9, wherein the coupling fluid is water.

23. The method of inspecting the part of claim 16, wherein controlling the coupling fluid source to direct coupling fluid upward to at least the particular elevation includes controlling the coupling fluid source to direct water upward to at least the particular elevation.

* * * * *